United States Patent [19]
Prescher et al.

[11] Patent Number: 4,751,332
[45] Date of Patent: Jun. 14, 1988

[54] PROCESS FOR THE PRODUCTION OF TRIHYDROXY-AND/OR ALKOXY-HYDROXYBENZENES

[75] Inventors: Guenter Prescher; Gebhard Ritter, both of Hanau; Holger Sauerstein, Grosskrotzenburg, all of Fed. Rep. of Germany

[73] Assignee: Degussa Aktiengesellschaft, Frankfurt, Fed. Rep. of Germany

[21] Appl. No.: 95,706

[22] Filed: Sep. 14, 1987

[30] Foreign Application Priority Data

Sep. 20, 1986 [DE] Fed. Rep. of Germany ....... 3632075

[51] Int. Cl.$^4$ ............................................. C07C 37/60
[52] U.S. Cl. ..................... 568/771; 560/70; 560/86; 562/476; 562/478; 568/650; 568/712; 568/763; 568/765; 568/774; 568/801; 568/803
[58] Field of Search ............... 568/803, 801, 771, 763, 568/765, 712, 801, 774; 562/476, 478; 560/86, 70

[56] References Cited

U.S. PATENT DOCUMENTS

| | | | |
|---|---|---|---|
| 4,066,707 | 1/1978 | Nakatani et al. | 568/803 |
| 4,324,925 | 4/1982 | Jupe et al. | 568/771 |
| 4,387,252 | 6/1983 | Jupe et al. | 568/771 |

FOREIGN PATENT DOCUMENTS 0027593  4/1981  European Pat. Off. ............ 568/771

*Primary Examiner*—Werren B. Lone
*Attorney, Agent, or Firm*—Beveridge, DeGrandi & Weilacher

[57] ABSTRACT

Resorcinol and substituted resorcinols are converted in one single step reaction into 1,2,3- and 1,2,4-trihydroxybenzenes and substituted hydroxy resorcinol compounds with a benzene solution of peroxypropionic acid.

11 Claims, No Drawings

PROCESS FOR THE PRODUCTION OF TRIHYDROXY-AND/OR ALKOXY-HYDROXYBENZENES

The invention relates to the production of trihydroxy- and alkoxy-hydroxybenzenes by hydroxylation of a starting compounds having one hydroxyl group less by means of peroxypropionic acid in benzene.

BACKGROUND AND PRIOR ART

Trihydroxy- and alkoxy-hydroxybenzenes are important structural components for the synthesis of pharmaceutical and cosmetic products, as well as for agro- and photo-chemicals (Kirk Othmer, Encyclopedia Chem. Technol., 3d edition, Vol. 18, page 670-84, 1982).

Until this time these compounds could be produced only at great cost and in several process steps.

For example, in European Patent No. 25 659, there is described a method of producing pyrogallol and substituted pyrogallol compounds by first of all transforming into suitable chlorine compounds by chlorination of the 2,6-dimethyl phenol derivative starting materials, and thereafter converting the chloromethylene groups thereof into aldehydes. The aldehydes were then oxidized in an alkaline medium into the corresponding pyrogallol and substituted pyrogallol compounds in accordance with the Dakin reaction, with peroxy compounds, such as hydrogen peroxide or peroxy acides, or their salts. However, this multistep process led to only moderate yields despite the considerable outlay.

Another process involving many steps is a modified Dakin reaction, which was carried out over the corresponding hydroxybenzaldehyde, and which led to satisfactory yields only if the pH level during the reaction was held continuously at 6-7 by addition of bases. Then the work up was also difficult in this process (European Patent No. 44 260).

Another complicated process with very variable yields of pyrogallol or pyrogallol compounds is disclosed in German OLS No. 26 53 446. A 2,2,6,6-tetrahalogen cyclohexanon must be produced first, which is then hydrolyzed with water in the presence of a catalyst or in the form of an alkoxide with acids.

Additional attempts using diaminophenols to obtain polyhydroxyl compounds did not lead to good results and were quite costly (German OLS No. 24 43 336).

Another possibility of obtaining hydroxy hydroquinone or substituted polyhydroxy compounds by means of the Thiele-Winter reaction was both very complicated and technically costly. The reaction actually consists of the conversion of a suitable quinone into a hydroxy-hydroquinone by acetoxylation with acetic acid anhydride in the presence of sulfuric acid or boron trifluoride etherate to the corresponding triacetate and then its conversion into the desired hydroxy hydroquinone or into substituted polyhydroxy compounds (German OLS No. 24 59 059).

Until this time, the preparation of 2,6-dimethoxy phenol occurred as a result of complete methylation of gallic acid, subsequent decarboxylation and selective demethylation of the 2-methoxy function. The 2,6-dimethoxyphenol yield was low, since only a 50% yield could be obtained in the first step of the decarboxylation (J. Am. Chem. Soc. 72, 1950, page 4986). Another process is described in the literature to be found in J. Org. Chem. 1984, 49, 4740 and J. Chem. Soc. Perkin Trans. I 1974, page 1353.

With the heretofore known process aromatic aldehyde compounds are reacted through a Baeyer-Villiger oxidation into the desired phenols with hydrogen peroxide or peroxy acids. Although fairly good yields can be obtained with this process, the disadvantage has been noted of a very long reaction time, actually up to 14 or 16 hours. In addition, this process also requires many steps.

SUMMARY OF THE INVENTION

Therefore it is an object of the invention to provide a method to come directly to the corresponding trihydroxy-compounds or alkoxy-hydroxybenzenes starting from resorcinol and substituted resorcinols.

It has now been established that this can be attained by reacting resorcins represented by the following structural formula:

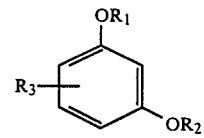

wherein
$R_1$ and $R_2$ represents hydrogen, aliphatic saturated or branched hydrocarbon groups with 1-9 carbon atoms, which can be the same or different,
$R_3$ represents hydrogen or the group —COOH, —COOR$_4$, —CH$_2$—OR$_4$, —SO$_3$H, —NO$_2$, —NH$_2$, —F, —Cl, Br, —I or R$_1$, wherein R$_4$ has the same meaning as R$_1$, with a solution of peroxypropionic acid in benzene in the mole ratio of 2:1 to 20:1 (resorcinol of the above formula to peroxypropionic acid) at a temperature of 20° to 140° C.

Peroxypropionic acid solutions in benzene may be obtained in accordance with the process described in German Patent No. 25 19 289. These solutions can indeed be still further purified as shown in German Patent 25 19 290 and can be used in this form; but raw benzene extracts obtained from the production of the peroxypropionic acid are preferred, which contain still more propionic acid, hydrogen peroxide and mineral acid, preferably sulfuric acid. The concentrations of the peroxypropionic acid in the benzene solutions lie in the range of 2 and 60% by weight, preferably in the range of 10 to 30% by weight. If the raw extract is used, then it can contain up to 1.5% by weight hydrogen peroxide; 1.5% by weight water and up to 800 ppm mineral acid. The propionic acid content of this raw extract is generally up to 13% by weight, although somewhat higher propionic acid contents can be used and do not cause damage either during implementation of the reaction or with the subsequent treatment of the reaction mixture.

In addition to resorcin itself, other substances which are suitable for the process according to the invention are especially 2-methylresorcinol, 5-methylresorcinol (orcin), 4n-hexylresorcinol, 4-t-butylresorcinol, 4-chlororesorcinol, dihydroxy benzoic acid, resorcinoldimethylether, resorcinolmonomethylether and resorcinoldiethylether. Especially preferred substances are resorcinol, resorcinol dimethyl ether, and also dihydroxybenzoic acid or 2-methyl resorcinol.

The resorcinols and substituted resorcinol compounds which are to be used are generally of commercial purity. If they are solid, they are used as melts, insofar as their melting point is sufficiently low that with benzene solutions of peroxypropionic acid they form no mixtures of questionable safety. The high melting point resorcinols on the other hand are dissolved with organic solvents and brought to reaction in liquid phase. Traditional solvents that can be used for this purpose include aliphatic carboxylic acid esters, for instance methyl-, ethyl-, n-propyl-, n-butyl-and isopropyl esters of acetic acid can be used as well as acetonitrile and chlorinated hydrocarbons. Others will be apparent to those skilled in the art.

A preferred mole ratio of the resorcinol to peroxypropionic acid is 2.5 to 10:1. Preferred reaction temperatures are between 30° and 120° C.

The pressure is not critical for the running of the reaction of this invention. It is preferred to conduct the reaction at ordinary atmospheric pressure, although it is possible to run at reduced or increased pressure as may be convenient.

A technical advantage of the process according to the present invention resides in being able to use commercial starting materials and obtain good yields in a single step reaction, to produce the desired 1, 2, 3 and 1, 2, 4-trihydroxybenzenes, and/or substituted hydroxy resorcinol compounds.

In accordance with the present invention it is possible to obtain in a single reaction step, pyrogallol and hydroxy hydroquinone, as well as 2,6-dimethoxyphenol and 2,4-dimethoxyphenol. The peroxypropionic acid conversions are very high, and often quantitative. The yields are likewise considerably higher than those of the known processes.

DETAILED DESCRIPTION OF THE INVENTION

The invention is described and illustrated in the following non-limiting examples:

EXAMPLE 1

(Mole ratio of resorcinol to peroxypropionic acid=20:1)

55 g (0.5 mole) of resorcinol are heated to 110° C. In a period of 15 minutes, 10 g of 22% by weight peroxypropionic acid (0.025 mole) in benzene are added to this melt with stirring. The temperature then rises to 120° C. After subsidence of the exothermic reaction and after 30 minutes a 100% peroxypropionic acid conversion reaction is analyzed. The reaction mixture then contains 1.6 g hydroxyhydroquinone and 1.27 g pyrogallol, which corresponds to a total yield of 91%, based upon the amount of peroxypropionic acid which is used.

EXAMPLE 2

(Mole ratio of resorcinol to peroxypropionic acid=10:1)

55 g (0.5 mole) of resorcinol are heated to 110° C. In a period of 15 minutes, 20.5 g of 22% by weight peroxypropionic acid (0.051 mole) in benzene are added into this melt with stirring. The temperature then rises to 120° C. After subsidence of the exothermic reaction and after 30 minutes a 100% peroxypropionic acid reaction is analyzed. The reaction mixture then contains 4.85 g hydroxy hydroquinone and 1.16 g pyrogallol, which corresponds to a total yield of 95%, based upon the amount of peroxypropionic acid which is used.

EXAMPLE 3

(Mole ratio of resorcinol to peroxypropionic acid=5:1)

55 g (0.5 mole) of resorcinol are heated to 110° C. In a period of 25 minutes, 42 g of 22% by weight peroxypropionic acid in benzene are added to this melt with stirring. The temperature then rises to 120° C. After subsidence of the exothermic reaction and after 45 minutes a 100% peroxypropionic acid reaction conversion is analyzed. The reaction mixture then contains 9.2 g hydroxy hydroquinone and 2.5 g pyrogallol, which corresponds to a total yield of 92%, based upon the amount of peroxypropionic acid which is used.

EXAMPLE 4

(Mole ratio of resorcinol to peroxypropionic acid=2.5:1)

27.5 g (0.25 mole) of resorcinol are heated to 110° C. In a period of 25 minutes, 41.0 of 22% by weight peroxypropionic acid in benzene are added to this melt with stirring. As a result of the addition of the peroxy acid, the temperature rises within 2 minutes to 115° C. and then after 4 minutes drops to 90° C. After 60 minutes a 100% peroxypropionic acid reaction conversion is analyzed. The reaction mixture then contains 6.95 g hydroxy hydroquinone and 2.4 g pyrogallol, which corresponds to a total yield of 74%, based upon the amount of peroxypropionic acid which is used.

EXAMPLE 5

(Mole ratio of resorcinol to peroxypropionic acid=10:1; resorcin is in a methanol solution)

55 g (0.5 mole) of resorcinol are dissolved in 16 ml methanol at 80° C. 20.4 g of 22% by weight peroxypropionic acid (0.05 mole) in benzene are added to this solution with stirring. The temperature then rises to 90° C. After subsidence of the exothermic reaction and after 60 minutes a 100% peroxypropionic acid reaction conversion is analyzed. The reaction mixture then contains 4.8 g hydroxy hydroquinone and 1.0 g pyrogallol, which corresponds to a total yield of 92%, based upon the amount of peroxypropionic acid which is used.

EXAMPLE 6

(Mole ratio of resorcinol dimethyl ether to peroxypropionic acid=10:1)

69 g (0.50 mole) of resorcinol dimethyl ether are heated to 30° C. In a period of 25 minutes, 20.4 g of 22% by weight peroxypropionic acid (0.05 mole) in benzene are added to this liquid with stirring. After 45 minutes of reaction, a 100% peroxypropionic acid reaction conversion is analyzed. The reaction mixture then contains 4.0 g of 2,4-dimeth oxyphenol and 1.5 g of 2,6-dimeth oxyphenol, which corresponds to a total yield of 70.5%, based upon the amount of peroxypropionic acid which is used.

Further variations and modifications of the invention will be apparent from the foregoing description and are intended to be encompassed by the claims appended hereto.

The German priority document No. P 36 32 075.7 is relied on and incorporated by reference.

We claim:

1. A process for the production of substituted 1,2,3- and 1,2,4-trihydroxybenzenes, comprising reacting a compound represented by the structural formula:

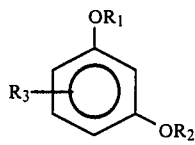

wherein
R$_1$ and R$_2$ are hydrogen, aliphatic saturated or branched hydrocarbon groups with 1-9 carbon atoms, which can be the same or different, and R$_3$ is hydrogen, COOH, —COOR$_4$, —CH$_2$—OR$_4$, —SO$_3$H, —NO$_2$, —NH$_2$, —F, —Cl, —Br, —I or R$_1$, in which R$_4$ has the same meaning as R$_1$ with a solution of peroxypropionic acid in benzene in a mole ratio of 2:1 to 20:1 (resorcinol of the above formula to peroxypropionic acid).

2. The process as in claim 1 wherein the reaction is carried out at about 20° to 140° C.

3. The process as in claim 1, wherein pure resorcinol is used.

4. The process as in claim 3 wherein resorcinol is used in the form of a melt.

5. The process as in claim 1, wherein said compound is 2-methyl resorcinol, 5-methyl resorcinol (orcin), 4n-hexylresorcinol, 4-t-butyl resorcinol, 4-chlororesorcinol, dihydroxybenzoic acid, resorcinol dimethyl ether, resorcinol monomethyl ether, or resorcinol diethyl ether.

6. The process as in claim 1 wherein said compound is resorcinol dimethyl ether, dihydroxybenzoic acid or 2-methyl resorcinol.

7. The process as in claim 1 wherein a benzene solution of peroxypropionic acid with a peroxypropionic acid content of 2-60% by weight, is used.

8. The process as in claim 7 wherein the peroxypropionic acid content is 10 to 30% by weight.

9. The process as in claim 1 wherein a peroxypropionic acid solution with a maximum content of 1.5% by weight hydrogen peroxide, 1.5% by weight water and up to 800 ppm mineral acid is used.

10. The process as in claim 1 wherein said compound and peroxypropionic acid are added in a mole ratio of 2.5 to 10.

11. The process as in claim 1 wherein the reaction is carried out at 30°-120° C.

* * * * *